(12) United States Patent
Roessle

(10) Patent No.: US 9,549,569 B2
(45) Date of Patent: Jan. 24, 2017

(54) NUTRITION FOR OBESE PATIENTS

(71) Applicant: NESTEC S.A., Vevey (CH)

(72) Inventor: Claudia Roessle, Morges (CH)

(73) Assignee: Nestec S.A., Vevey (CH)

( * ) Notice: Subject to any disclaimer, the term of this patent is extended or adjusted under 35 U.S.C. 154(b) by 55 days.

(21) Appl. No.: 14/053,192

(22) Filed: Oct. 14, 2013

(65) Prior Publication Data

US 2014/0051627 A1 Feb. 20, 2014

Related U.S. Application Data

(63) Continuation of application No. 12/064,686, filed as application No. PCT/EP2006/065562 on Aug. 22, 2006, now abandoned.

(30) Foreign Application Priority Data

Aug. 26, 2005 (EP) ..................................... 05018626
Nov. 9, 2005 (EP) ..................................... 05110556

(51) Int. Cl.
*A23L 1/303* (2006.01)
*A23L 1/29* (2006.01)

(52) U.S. Cl.
CPC ................ *A23L 1/293* (2013.01); *A23L 33/15* (2016.08); *A23L 33/16* (2016.08); *A23L 33/19* (2016.08); *A23L 33/30* (2016.08); *A23L 33/40* (2016.08); *A23V 2002/00* (2013.01)

(58) Field of Classification Search
CPC .......... A23L 1/296; A23L 1/302; A23L 1/304; A23V 2250/5452
USPC ...... 426/658, 72, 73, 74, 615, 656, 601, 810
See application file for complete search history.

(56) References Cited

U.S. PATENT DOCUMENTS 5,968,896 A * 10/1999 Bell ...................... A23L 1/296
514/168
2002/0142025 A1 10/2002 Hageman
2004/0097404 A1 5/2004 Kessler et al.
2004/0258826 A1 12/2004 Navarro Y Koren et al.
2005/0002988 A1 1/2005 Mizumoto et al.
2005/0147665 A1 7/2005 Horrobin et al.
2005/0233045 A1 10/2005 Aldred et al.

FOREIGN PATENT DOCUMENTS

| EP | 1302111 | 4/2003 |
|----|---------|--------|
| JP | H1071 | 1/1998 |
| JP | 2001120227 | 5/2001 |
| WO | 2004105520 | 12/2004 |

OTHER PUBLICATIONS

"Obesity Action Coalition", http?//www.obesityaction.org/educational-resources/resource-articles-2/weight-loss-suger . . .Feb. 23, 2016, pp. 1-3.*
Malinowski SS, Am J Med Sci, Apr. 2006:331(4):2191-25 (abstract).*
"Pre-OpWeight Loss Surgery Diet", http://www.wlshelp.com/pre-weight-loss-surgery=diet.html , 2002, pp. 1-5.*
International Search Report and Written Opinion received for International Application No. PCT/EP2006/065562 filed on Aug. 22, 2006.
Japanese Office Action for Japanese Application No. P2008-527464 mailed Feb. 15, 2011.
Dickerson et al. "Hypocaloric Enteral Tube Feeding in Critically Ill Obese Patients" Nutrition, 2002, vol. 18, pp. 241-246.
European Office Action for Application No. 06 841 257.6-1358, dated Jun. 2, 2015, 7 pages.

* cited by examiner

*Primary Examiner* — Helen F Heggestad
(74) *Attorney, Agent, or Firm* — K&L Gates LLP

(57) ABSTRACT

The invention provides a composition and method for providing nutritional support to obese patients. The composition has an energy density between 0.4 and 0.9 kcal/ml and comprises a protein source which comprises at least 30% by weight whey protein and provides at least 30% of the total calories of the composition. The composition may include a carbohydrate source and a lipid source. Preferably at least 50% by weight of the protein source is whey protein. The invention further extends to use of the composition in the prevention of treatment of malnutrition in obese patients.

20 Claims, No Drawings

NUTRITION FOR OBESE PATIENTS

PRIORITY CLAIM

This application is a continuation application of U.S. patent application Ser. No. 12/064,686, filed on Jun. 30, 2008, which claims priority to PCT/EP2006/065562, filed on Aug. 22, 2006, which claims priority to EP05018626.1, filed on Aug. 26, 2005, and EP05110556.7, filed on Nov. 9, 2005, the entire disclosure of which is incorporated herein by reference.

BACKGROUND

This invention relates generally to compositions and methods for the treatment and nutritional support of patients. More specifically, this invention relates to the nutritional support of obese patients prior to, during and after hospitalisation for surgery, treatment of diseases or other disorders as well as during periods of convalescence.

The prevalence of obesity in adults, children and adolescents has increased rapidly over the past 30 years in the United States and globally and continues to rise. Obesity is classically defined based on the percentage of body fat or, more recently, the body mass index or BMI. The BMI is defined as the ratio of weight in Kg divided by the height in meters, squared. As obesity becomes more prevalent in all age groups, it is inevitable that the number of patients in hospitals who are also obese will increase.

Many obese patients have pre-existing chronic diseases related to their obesity such as impaired glycaemic control, diabetes mellitus, coronary artery disease, hypertension, respiratory abnormalities, hyperlipidaemia, degenerative joint disease, and hepatobiliary disease that are likely to complicate even routine hospital care. In addition, obese patients are more likely than their non-obese counterparts to develop postoperative complications such as impaired wound-healing, nosocomial infections, respiratory complications, and delayed cardiac recuperation. In adult intensive care patients, obesity (BMI greater than 30) has even been reported to be significantly associated with increased risk of mortality. Obesity entails increased oxidative stress and, in many cases, sarcopenia. It is well known that acute illness and/or surgical intervention is also associated with oxidative stress as well as negative nitrogen balance and loss of muscle mass, and in many cases insulin resistance is enhanced. In other words, acute illness is likely to exacerbate physiological and metabolic alterations already present at baseline in obese patients.

Recently, Dickerson et al (Nutrition 18:241-246 2002) compared the effects of hypocaloric and eucaloric enteral tube feeding in critically ill obese patients. Their results suggested that hypocaloric enteral nutritional support (by which the authors meant feeding a composition with an energy density of at least 1.0 kcal/ml) was at least as effective as eucaloric feeding in this group. In the more generalised group of obese patients who, although ill, are not critically ill, there is a tendency for the nutrition offered post operatively in particular to be less than ideal. These patients tend to be offered either the same feeds as non-obese patients and thus ingest calories they do not require. Alternatively, it is assumed that in the short term no nutritional support at all is needed because the patients are calorically abundant. However, this overlooks the possibility that, when stressed for example by illness or surgery, obese patients may suffer from protein and micronutrient depletion just as non-obese patients do. Further, as noted above, obese patients are at greater risk of postoperative complications and would be in better conditions to resist these complications if they were not further weakened by impaired nutritional status. A need therefore exists for a nutritional composition designed to meet the nutritional needs of patients who are obese.

SUMMARY OF THE INVENTION

In a first aspect, this invention provides the use of a protein source, Vitamin A, Vitamin C, Vitamin E, zinc and selenium in the manufacture of a composition for the prevention or treatment of malnutrition in an obese patient wherein the composition has an energy density between 0.4 and 0.9 kcal/ml and comprises per liter at least 500 µg RE of Vitamin A, 70 mg of Vitamin C, 9.0 mg α TE of Vitamin E, 4.0 mg zinc and 30 mg selenium and the protein source comprises at least 30% by weight whey protein and provides at least 30% of the total calories of the composition.

In a second aspect, this invention provides a nutritional composition for the prevention or treatment of malnutrition in an obese patient which composition has an energy density between 0.4 and 0.9 kcal/ml and comprises per liter at least 500 µg RE of Vitamin A, 70 mg of Vitamin C, 9.0 mg α TE of Vitamin E, 4.0 mg zinc and 30 mg selenium and a protein source which provides at least 30% of the total calories of the composition wherein at least 30% by weight of the protein source is whey protein.

In a third aspect, this invention provides the use of a protein source, a carbohydrate source, and a lipid source in the manufacture of a composition for the prevention or treatment of malnutrition in an obese patient wherein the composition has an energy density between 0.4 and 0.9 kcal/ml and the protein source comprises at least 30% by weight whey protein and provides at least 30% of the total calories of the composition.

In a fourth aspect, this invention provides a nutritional composition for the prevention or treatment of malnutrition in an obese patient which composition has an energy density between 0.4 and 0.9 kcal/ml and comprises a protein source which provides at least 30% of the total calories of the composition, a carbohydrate source and a lipid source wherein at least 30% by weight of the protein source is whey protein.

In a fifth aspect, this invention provides a method of preventing or treating malnutrition in an obese patient in need thereof by administering a therapeutic amount of a nutritional composition comprising a protein source wherein the composition has an energy density between 0.4 and 0.9 kcal/ml and the protein source comprises at least 30% by weight of whey protein and provides at least 30% of the total calories of the composition.

Preferably whey protein constitutes at least 50% of the protein source, more preferably from 60 to 85% of the protein source.

In the event that the nutritional composition comprises a source of carbohydrates and a source of lipids, the protein source may provide 30 to 65% of the total calories of the composition, preferably from 35 to 50% and more preferably 40 to 50% of the total calories of the composition.

The composition may be a nutritional supplement, that is, nutritionally incomplete and intended to be consumed in addition to other foodstuffs or it may be nutritionally complete, including a carbohydrate source and a lipid source in addition to the protein source. It may be formulated as a ready to consume liquid for sip feeding or tube feeding, as a powdered composition which may be reconstituted with water prior to being fed orally or administered by tube feeding, as a semi-liquid food such as a spoonable dessert or in any other appropriate form e.g. bars, biscuits etc.

If present, the carbohydrate source may provide 20 to 50% of the total calories of the composition and preferably from 25 to 45% of the total calories of the composition.

If present, the lipid source may provide 10 to 40% of the total calories of the composition and preferably from 25 to 30% of the total calories of the composition.

DETAILED DESCRIPTION OF THE INVENTION

In this specification, the term "obese patient" means an individual who is obese i.e. with a BMI greater than 30 and who is undergoing or requires or is convalescing from therapy or surgery for a related or unrelated condition. Examples of "related conditions" include conditions that are thought to be linked with overweight and obesity such as development of metabolic syndrome and Type II diabetes.

References to components of the composition being present in a specified number of grams per liter refer in the context of powdered compositions to the composition after re-constitution.

Whey protein comprises at least 30% of the protein source in the composition of the invention, preferably at least 50% and more preferably from 60 to 85% of the protein source. Whey protein has fast gastric emptying and is associated with an increased satiety response so is suitable for a hypocaloric composition for obese patients. Further, it has been shown to stimulate insulin release in healthy subjects as well as those suffering from Type II diabetes and is thus a suitable protein source for individuals who may suffer from impaired glycaemic control. Whey protein has also been demonstrated to stimulate postprandial protein accretion; in particular in elderly subjects suggesting that protein losses can be limited by intake of whey protein. It is also a rich source of branched-chain amino acids which it is believed may be associated with the stimulation of protein synthesis. Further, whey protein is a rich source of cysteine which is a key constituent of glutathione, a major endogenous antioxidant. It has been shown that cysteine and glutathione are depleted in critically ill patients and that supplementation with cysteine can attenuate this depletion. Finally, whey protein is believed to have anti-inflammatory properties which may be of relevance in the treatment of conditions such as obesity which are thought to engender chronic low-level inflammation. The whey protein may be intact or partially or extensively hydrolysed. Mixtures of intact and hydrolysed whey proteins may be used.

The balance of the protein source may be any suitable protein such as defatted milk protein, soy protein or casein, in each case either in the intact form or hydrolysed. Mixtures of the above proteins may also be used as may mixtures of intact and hydrolysed proteins. Free amino acids such as Leucine may also be added.

The lipid source if present preferably does not contribute more than 40% of the total calories of the composition since the use of endogenous lipid stores should be stimulated in obese patients. Nevertheless, essential fatty acid intake should be considered.

A high intake of n-6 polyunsaturated fats should preferably be avoided where there is a risk of stress and inflammatory conditions. Preferably, the ratio of n6/n3 fatty acids should be between 2:1 and 6:1. These requirements can, for example, be met by using a blend of canola oil, corn oil and high-oleic acid sunflower oil supplemented with a source rich in n3 PUFA such as fish oil if a higher n3 content is required. The lipid source may also include medium chain triglycerides if required.

The nutritional composition of the present invention may contain a carbohydrate source. Preferably, the carbohydrate source should be slowly digested or metabolised independently of insulin, thus avoiding high post-prandial glycaemic peaks. Suitable carbohydrate sources are modified starches such as modified potato or tapioca starch, dextrins such as tapioca dextrin, isomaltulose, trehalose, tagatose, fructose and polyols such as xylitol and sorbitol as well as mixtures thereof. The composition may also contain minerals, micronutrients and trace elements in accordance with the recommendations of Government bodies such as the USRDA. Preferably the composition contains elevated amounts of Vitamins A, C, and E, zinc and selenium, for example, per liter at least:— 500 µg RE of Vitamin A, 70 mg of Vitamin C, 9.0 mg α TE of Vitamin E, 4.0 mg zinc and 30 mg selenium, more preferably per liter at least:— 1000 µg RE of Vitamin A, 125 mg of Vitamin C, 15.0 mg α TE of Vitamin E, 10.0 mg zinc and 100 mg selenium.

The composition preferably also contains elevated amounts of iron, calcium, folate, Vitamin B12, Vitamin D and Vitamin K, for example, per liter at least 6 mg iron, 500 mg calcium, 160 mg folate, 2.0 µg Vitamin B12, 8 µg Vitamin D and 60 µg Vitamin K.

The composition may further contain a source of dietary fibre. Dietary fibre passes through the small intestine undigested by enzymes and functions as a natural bulking agent and laxative. Dietary fibre may be soluble or insoluble and in general a blend of the two types is preferred. Suitable sources of dietary fibre include soy, oat and gum Arabic and mixtures thereof. A particularly preferred fibre blend is a mixture of outer pea fibre (predominantly insoluble), inner pea fibre, acacia gum and short chain fructo-oligosaccharides (all soluble). Preferably, if fibre is present the fibre content is between 10 and 40 g/l.

The composition may be manufactured in any suitable manner. For example, the composition may be manufactured by blending together the protein source, the carbohydrate source (if present), and the lipid source (if present) in appropriate proportions. If used, emulsifiers may be included in the blend at this stage. The vitamins and minerals may be added at this point but are usually added later to avoid thermal degradation. Any lipophilic vitamins, emulsifiers and the like may be dissolved into the lipid source prior to blending. Water, preferably water which has been subjected to reverse osmosis, may then be mixed in to form a liquid mixture.

The liquid mixture may then be thermally treated to reduce bacterial loads. For example, the liquid mixture may be rapidly heated to a temperature in the range of about 80° C. to about 110° C. for about 5 seconds to about 5 minutes. This may be carried out by steam injection or by heat exchanger; for example a plate heat exchanger The liquid mixture may then be cooled to about 60° C. to about 85° C.; for example by flash cooling. The liquid mixture may then be homogenised; for example in two stages at about 7 MPa to about 40 MPa in the first stage and about 2 MPa to about 14 MPa in the second stage. The homogenised mixture may then be further cooled and any heat sensitive components; such as vitamins and minerals may be added. The pH and solids content of the homogenised mixture is conveniently standardised at this point.

If it is desired to produce a powdered composition, the homogenised mixture is transferred to a suitable drying apparatus such as a spray drier or freeze drier and converted to powder. The powder should have a moisture content of less than about 5% by weight.

If it is desired to produce a liquid composition, the homogenised mixture is filled into suitable containers; preferably aseptically. However, the composition may also be retorted in the container. Suitable apparatus for carrying out filling of this nature is commercially available. The composition may be in the form of a ready to feed product having a solids content of about 10 to about 14% by weight or may be in the form of a concentrate; usually of solids content of about 20 to about 26% by weight.

Alternatively, to prepare a liquid composition based on intact whey proteins, whey protein isolate may be dissolved in demineralised water. After complete dissolution of the protein, the carbohydrate is added to the protein solution. After complete dissolution of the carbohydrate, the pH is adjusted to 3.0 at ambient temperature. The resulting solution is heat sterilised (e.g. UHT), cooled and the pH is adjusted to 6.8 under aseptic conditions Meanwhile, a dispersion of defatted milk protein concentrate and tri-calcium-citrate in demineralised water is prepared. The fat mix is warmed to 70° C. and monodiglycerides are dissolved in the fat. The fat mix is emulsified together with the protein dispersion using a colloidal mill. The resulting coarse emulsion is homogenised at 200 bar/40 bar at ca 65° C. The minerals, trace elements and vitamins are then added to the emulsion and its pH is adjusted to 6.8. The resulting emulsion is UHT sterilised, flash-cooled to 70° C. and then aseptically homogenised. The emulsion is cooled to about 10° C. and pumped to a sterile tank where it is mixed with the protein/carbohydrate phase. After thorough mixing in the tank, the sterile composition is filled aseptically into the desired container

Example 1

Two examples of complete nutritional compositions for sip feeding according to the present invention are given below. The compositions are given by way of illustration only.

The compositions include the following ingredients: protein: whey protein (50% by weight of total protein), defatted milk protein; carbohydrate: modified tapioca and corn starch; fat: about 50% canola oil, about 20% corn oil, about 30% higholeic sunflower oil, n6:n3 ratio about 5; fibre (inner pea fibre, outer pea fibre and fructo-oligosaccharides); water; vitamin A; vitamin C vitamin D; vitamin E; vitamin K; vitamin $B_1$; Vitamin $B_2$; vitamin $B_6$; niacin; folic acid; pantothenic acid; vitamin $B_{12}$; biotin; calcium; magnesium; zinc; iron; copper; manganese; iodine; sodium; potassium; chloride; chromium; molybdenum; fluoride and selenium.

The compositions have the following nutrient profiles (per 200 ml serving):

| Nutrient Composition | Example A | Example B |
|---|---|---|
| Caloric Density | 0.5 kcal/ml | 0.75 kcal/ml |
| Protein (g) | 12 | 15 |
| Carbohydrate (g) | 6.8 | 11.25 |
| Fat (g) | 2.8 | 5 |
| Dietary Fibre (g) | 5.2 | 5.2 |
| Vitamin A(μg RE) | 210 | 210 E |
| Vitamin D(μg) | 2.6 | 2.6 |
| Vitamin E (mg αTE) | 3.2 | 4.5 E |
| Vitamin K(μg) | 13.8 | 13.8 |
| Vitamin C (mg) | 26 | 26 |
| VitaminB1 (mg) | 0.3 | 0.3 |

-continued

| Nutrient Composition | Example A | Example B |
|---|---|---|
| Vitamin B2 (mg) | 0.36 | 0.36 |
| Niacin (mg) | 3.0 | 3.0 |
| Vitamin B6 (mg) | 0.42 | 0.42 |
| Folic Acid(g) | 60 | 60 |
| Pantothenic Acid (mg) | 1.2 | 1.2 |
| Vitamin B12(μg) | 0.7 | 1.0 |
| Biotin (μg) | 7.5 | 12 |
| Calcium (mg) | 240 | 240 |
| Magnesium (mg) | 40 | 40 |
| Zinc (mg) | 2.4 | 2.4 |
| Iron (mg) | 2.0 | 2.0 |
| Copper(mg) | 0.24 | 0.24 |
| Manganese (mg) | 0.5 | 0.5 |
| Iodine (J-lg) | 20 | 20 |
| Sodium (mg) | 70 | 70 |
| Potassium (mg) | 260 | 260 |
| Chloride (mg) | 140 | 140 |
| Chromium (J-lg) | 12.4 | 12.4 |
| Molybdenum ( )-lg) | 15 | 15 |
| Selenium (J-lg) | 12.6 | 12.6 |
| Fluoride (mg) | 0.2 | 0.2 |

Example 2

Two examples of liquid tube feeding compositions according to the present invention are given below. The compositions are given by way of illustration only.

The compositions include the following ingredients: protein: hydrolysed whey protein (50% by weight of total protein), potassium caseinate; soy protein isolate; carbohydrate: modified tapioca and corn starch; fat: about 50% canola oil, about 20% corn oil, about 30% high-oleic sunflower oil, n6:n3 ratio about 5; fibre (inner pea fibre, outer pea fibre, acacia gum and :fructo-oligosaccharides); water; vitamin A; vitamin C vitamin D; vitamin E; vitamin K; vitamin B1; Vitamin B2; vitamin B6; niacin; folic acid; pantothenic acid; vitamin B12; biotin; calcium; magnesium; zinc; iron; copper; manganese; iodine; sodium; potassium; chloride; chromium; molybdenum; fluoride and selenium.

The compositions have the following nutrient profiles (per 1500 ml):

| Nutrient Composition | Example C | Example D |
|---|---|---|
| Caloric Density | 0.5 kcal/ml | 0.75 kcal/ml |
| Protein (g) | 84 | 100 |
| Carbohydrate (g) | 47 | 124 |
| Fat (g) | 25 | 37.5 |
| Dietary Fibre (g) | 22.5 | 22.5 |
| Vitamin A (μg RE) | 1950 | 1950 |
| Vitamin D (μg) | 22.5 | 22.5 |
| Vitamin E (mg αTE) | 30 | 30 |
| Vitamin K (μg) | 124.5 | 124.5 |
| Vitamin C (mg) | 225 | 225 |
| Vitamin B1 (mg) | 2.7 | 2.7 |
| Vitamin B2 (mg) | 3.0 | 3.0 |
| Niacin (mg) | 27 | 27 |
| Vitamin B6 (mg) | 3.9 | 3.9 |
| Folic Acid (μg) | 540 | 540 g |
| Pantothenic Acid (mg) | 11.25 | 11.25 |
| Vitamin B 12 (μg) | 6.75 | 6.75 |
| Biotin (μg) | 67.5 | 67.5 |
| Calcium (mg) | 1350 | 1350 |
| Magnesium (mg) | 450 | 450 |
| Zinc (mg) | 22.5 | 22.5 |
| Iron (mg) | 24 | 24 |
| Copper (mg) | 2.25 | 2.25 |
| Manganese (mg) | 4.95 | 4.95 |
| Iodine (μg) | 225 | 225 |

-continued

| Nutrient Composition | Example C | Example D |
|---|---|---|
| Sodium (mg) | 1350 | 1350 |
| Potassium (mg) | 2550 | 2550 |
| Chloride (mg) | 2100 | 2100 |
| Chromium (μg) | 112.5 | 112.5 |
| Molybdenum (μg) | 225 | 225 |
| Selenium (μg) | 112.5 | 112.5 |
| Fluoride (mg) | 2.25 | 2.25 |

The invention claimed is:

1. A method for treatment of malnutrition comprising the step of administering to an obese patient suffering from malnutrition a nutritional composition comprising an energy density between 0.4 and 0.9 kcal/ml and, per liter, at least 500 μg RE of Vitamin A, 70 mg of Vitamin C, 9.0 mg α TE of Vitamin E, 4.0 mg of zinc and 30 μg of selenium, and the composition comprises a protein source providing 35 to 50% of the total calories of the composition and comprising between 60 and 85% by weight whey protein, and the nutritional composition is nutritionally complete.

2. The method of claim 1, wherein the nutritional composition comprises, per liter, at least 1000 μg RE of Vitamin A, 125 mg of Vitamin C, 15.0 mg α TE of Vitamin E, 10.0 mg of zinc and 100 μg of selenium.

3. The method of claim 1, wherein the protein source provides 40 to 50% of the total calories of the composition.

4. The method of claim 1, wherein the nutritional composition further comprises a carbohydrate source that provides 25 to 45% of the total calories of the composition.

5. The method of claim 1, wherein the nutritional composition further comprises a lipid source that provides 25 to 30% of the total calories of the composition.

6. The method of claim 5, wherein a ratio of n6:n3 long chain polyunsaturated fatty acids in the lipid source is between 6:1 and 2:1.

7. The method of claim 1, wherein the nutritional composition further comprises from 10 to 40 g/l of dietary fiber.

8. The method of claim 1, wherein the nutritional composition further comprises, per liter, at least 6 mg iron, 500 mg calcium, 160 mg folate, 2.0 μg Vitamin B12, 8 μg Vitamin D and 60 μg Vitamin K.

9. The method of claim 1, wherein a remainder of the protein source is selected from the group consisting of defatted milk protein, soy protein, casein and combinations thereof.

10. A method for prevention or treatment of malnutrition comprising the step of administering a nutritional composition comprising an energy density between 0.4 and 0.9 kcal/ml and, per liter, at least 500 μg RE of Vitamin A, 70 mg of Vitamin C, 9.0 mg α TE of Vitamin E, 4.0 mg of zinc and 30 μg of selenium, and the composition comprises a protein source providing 35 to 50% of the total calories of the composition and comprising between 60 and 85% by weight whey protein, to an obese patient scheduled to undergo a treatment selected from the group consisting of surgery for a condition related to obesity and surgery for a condition unrelated to obesity.

11. The method of claim 10, wherein the obese patient is suffering from malnutrition.

12. The method of claim 10, wherein the condition related to obesity is Type II diabetes.

13. A method for prevention or treatment of malnutrition comprising the step of administering to an obese patient a nutritional composition comprising an energy density between 0.4 and 0.9 kcal/ml and, per liter, at least 500 μg RE of Vitamin A, 70 mg of Vitamin C, 9.0 mg α TE of Vitamin E, 4.0 mg of zinc and 30 μg of selenium, and the composition comprises a protein source providing 35 to 50% of the total calories of the composition and comprising between 60 and 85% by weight whey protein, and the nutritional composition is administered during hospitalization of the obese patient for a treatment selected from the group consisting of surgery for a condition related to obesity and surgery for a condition unrelated to obesity.

14. The method of claim 13, wherein the obese patient is suffering from malnutrition.

15. The method of claim 13, wherein the condition related to obesity is Type II diabetes.

16. A method for prevention or treatment of malnutrition comprising the step of administering a nutritional composition comprising an energy density between 0.4 and 0.9 kcal/ml and, per liter, at least 500 μg RE of Vitamin A, 70 mg of Vitamin C, 9.0 mg α TE of Vitamin E, 4.0 mg of zinc and 30 μg of selenium, and the composition comprises a protein source providing 35 to 50% of the total calories of the composition and comprising between 60 and 85% by weight whey protein, to an obese patient convalescing from a treatment selected from the group consisting of surgery for a condition related to obesity and surgery for a condition unrelated to obesity.

17. The method of claim 16, wherein the obese patient is suffering from malnutrition.

18. The method of claim 16, wherein the condition related to obesity is Type II diabetes.

19. The method of claim 16, wherein the treatment from which the obese patient is convalescing is surgery for a condition related to obesity.

20. The method of claim 16, wherein the treatment from which the obese patient is convalescing is surgery for a condition unrelated to obesity.

* * * * *